United States Patent [19]

Marrelli

[11] Patent Number: 5,546,007
[45] Date of Patent: Aug. 13, 1996

[54] MICROWAVE WATER CUT MONITORING MEANS AND METHOD

[75] Inventor: John D. Marrelli, Houston, Tex.

[73] Assignee: Texaco Inc., White Plains, N.Y.

[21] Appl. No.: 346,053

[22] Filed: Nov. 29, 1994

Related U.S. Application Data

[63] Continuation-in-part of Ser. No. 1,704, Jan. 7, 1993, abandoned.

[51] Int. Cl.$^6$ .................................................. G01N 22/04
[52] U.S. Cl. ...................... 324/640; 324/647; 324/698; 73/61.43; 73/61.44
[58] Field of Search .................... 324/439, 442, 324/446, 443, 639, 640, 647, 698; 73/195, 196, 863.31, 61.43, 61.44

[56] References Cited

U.S. PATENT DOCUMENTS

| | | | |
|---|---|---|---|
| 4,634,963 | 1/1987 | Lunden | 324/639 |
| 4,947,127 | 8/1990 | Helms | 324/640 |
| 5,101,163 | 3/1992 | Agar | 324/639 |

*Primary Examiner*—Kenneth A. Wieder
*Assistant Examiner*—Jose M. Solis
*Attorney, Agent, or Firm*—Kenneth R. Priem; James L. Bailey; William J. Beard

[57] ABSTRACT

Apparatus which determines the water cut of a sample petroleum stream irradiates the sample stream at two different locations with microwave energy. The distance that the microwave energies pass through the sample stream are also different. A receiver receives the microwave energies and provides corresponding received signals. The water cut is determined in accordance with the received signals.

5 Claims, 2 Drawing Sheets

MICROWAVE WATER CUT MONITORING MEANS AND METHOD

CROSS-REFERENCE TO RELATED APPLICATIONS

The present application is a continuation-in-part of my patent application Ser. No. 08/001,704, filed Jan. 7, 1993, now abandoned.

BACKGROUND OF THE INVENTION

The Field of the Invention

The present invention relates to water cut monitors in general and, more particularly, to microwave water cut monitors.

The Prior Art

SUMMARY OF THE INVENTION

Apparatus which determines the water cut of a sample petroleum stream irradiates the sample stream at two different locations with microwave energy. The distance that the microwave energies pass through the sample stream are also different. A receiver receives the microwave energies and provides corresponding received signals. The water cut is determined in accordance with the received signals.

The objects and advantages of the invention will appear more fully hereinafter from a consideration of the detailed description which follows, taken together with the accompanying drawing wherein one embodiment of the invention is illustrated by way of example. It is to be expressly understood, however, that the drawings are for illustration purposes only and are not to be construed as defining the limits of the invention.

BRIEF DESCRIPTION OF THE DRAWINGS

The present invention will now be described, by way of example, with reference to the accompanying drawings, in which.

DETAILED DESCRIPTION PREFERRED EMBODIMENT

Figure 1:
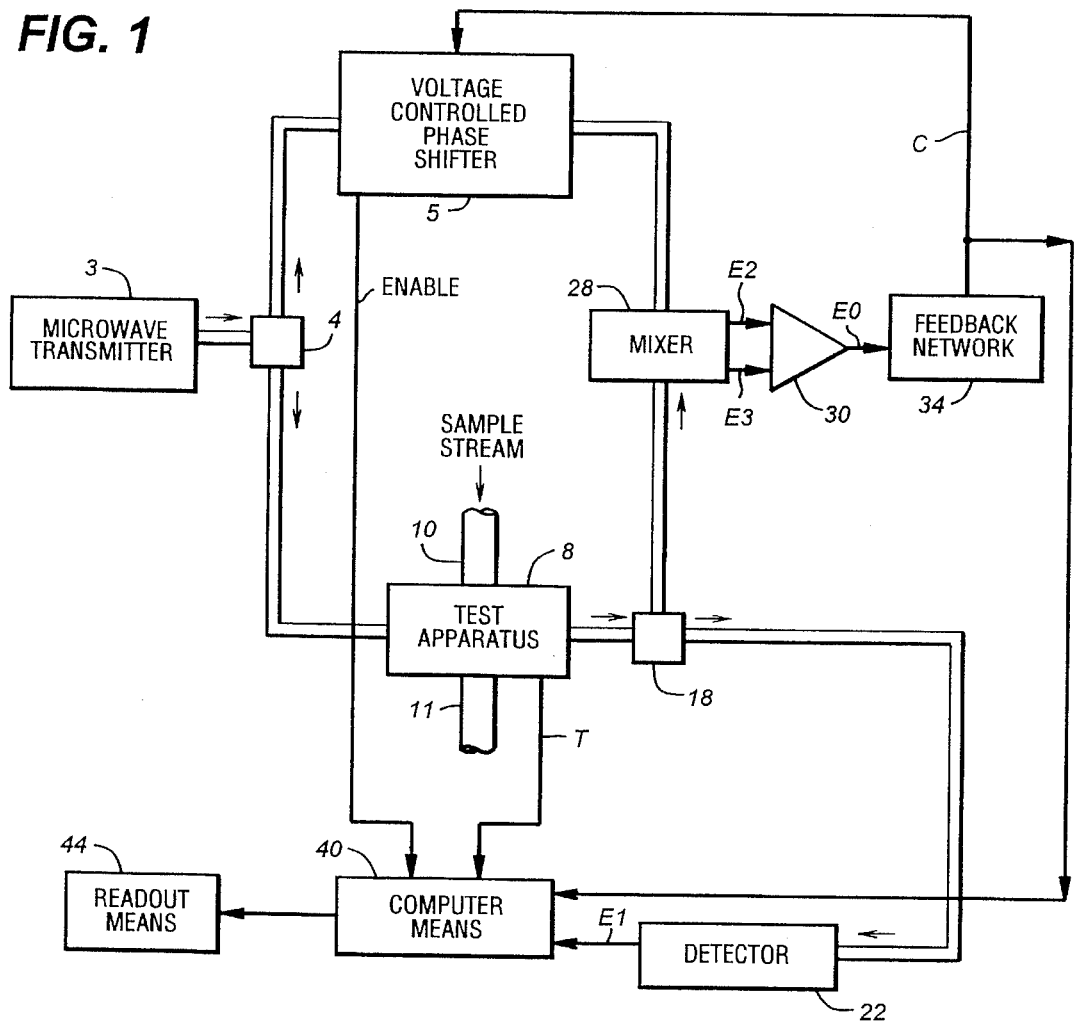
FIG. 1 is a simplified block diagram, which is partially schematic, of a microwave water cut monitor constructed in accordance with the present invention.

The water cut monitor shown in FIG. 1 includes a microwave transmitter 3 providing electromagnetic energy, hereinafter referred to as microwave energy, at a microwave frequency. Transmitter 3 is low powered and may use a microwave gun source. Transmitter 3 provides microwave energy to directional coupler 4. Directional coupler 4 provides microwave energy to a conventional type voltage controlled phase shifter 5 and to test apparatus 8. All conductance or carrying of microwave energy is accomplished by using conventional type waveguides and coaxial cables.

Test apparatus 8 has a line 10, carrying a sample stream of a multi-phase petroleum stream, entering apparatus 8. The sample stream leaves test apparatus 8 by way of a line 11. Apparatus 8 will be described in more detail hereinafter. Suffice to say at this point that microwave energy leaving test apparatus 8 in line 11, hereinafter referred to as test microwave energy, is microwave energy that has passed through the sample stream. The test microwave energy is applied to a directional coupler 18. Directional coupler 18 provides the test microwave energy to a detector 22 and to a mixer 28. Detector 22 provides a signal E1 corresponding to the power of the microwave energy received by antenna 14.

Voltage control phase shifter 5 provides microwave energy, hereinafter called the reference microwave energy, to mixer 28 which mixes the reference microwave energy and the test microwave energy to provide two electrical signals E2, E3, representative of the phases of the reference microwave energy and the test microwave energy, respectively.

A differential amplifier 30 provides an output signal E0 in accordance with the difference between signals E2 and E3. Signal E0 is a function of the phase difference between the reference microwave energy and the test microwave energy and is provided to a feedback network 34. Feedback network 34 provides a signal C to voltage control phase shifter 5, controlling the phase of the reference microwave energy, and to a mini-computer means 40. Signal E0, and hence signal C, decreases in amplitude until there is substantially 90° phase difference between the reference microwave energy and the test microwave energy. Voltage control phase shifter 5 indicates the amount of phase shift required to eliminate the phase difference.

Signals E2, T and C are provided to a conventional type mini-computer means 40 which contains within its memory means having data related to phase and power for various percentages of water cuts that could be encountered in the production stream. Phase shifter 5 also provides an enable signal to computer means 40 allowing computer means 40 to utilize signals T, C and E1 to select the proper water cut value computer means 40 provides signals, corresponding to the selected water cut value, to readout means 44 which may be either display means or record means or a combination of the two.

Figure 2:
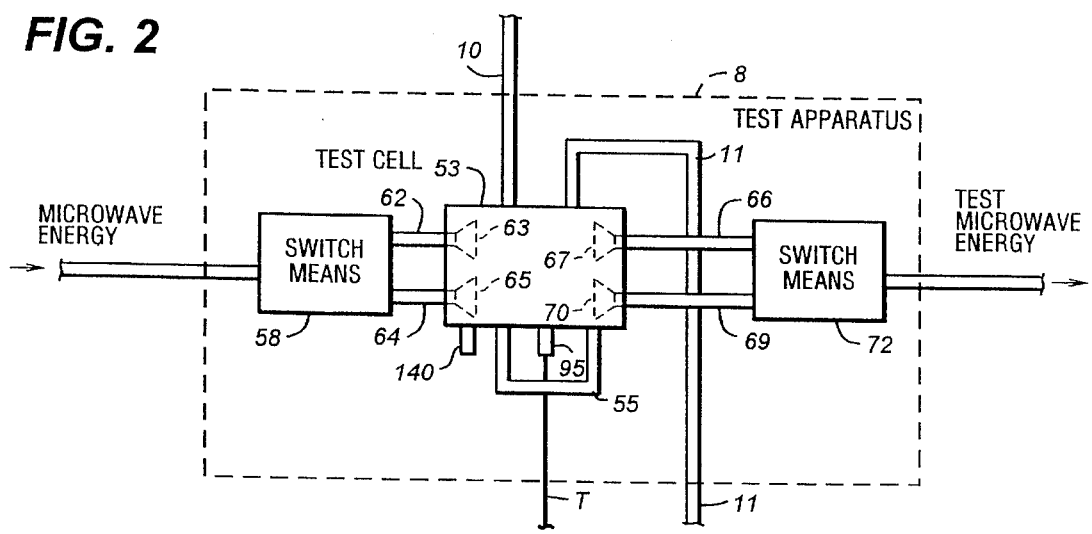
FIG. 2 is a simplified block diagram of the test apparatus shown in FIG. 1.

With reference to FIGS. 1 and 2, test apparatus 8 includes a test cell 53 receiving the sample stream from line 10 and providing it to a line 55. The sample stream in line 55 is provided to test cell 53. A channel in test cell 53 connects line 55 to line 11. Test cell 53 will be described more fully hereinafter.

Microwave energy from directional coupler 4 enters switch means 58 which provides microwave energy to test cell 53 through either a line 62 or a line 64. Line 62 provides the microwave to an antenna 63 which radiates the microwave energy into the sample stream. Similarly, when microwave energy is provided by line 64, it is provided to an antenna 65. Antenna 65 radiates the microwave energy into the sample stream. However, as explained hereinafter, the distance that the microwave energy travels through the sample stream varies dependent on which antenna 63 or 65 is radiating. Line 66 carries test microwave energy received by an antenna 67 after it has passed through the sample stream. Similarly, line 69 carries test microwave energy received by an antenna 70 after it has passed through the sample stream. Switch means 72 receives the test microwave energy from either line 66 or line 67 and provides it to directional coupler 18.

Figure 3:
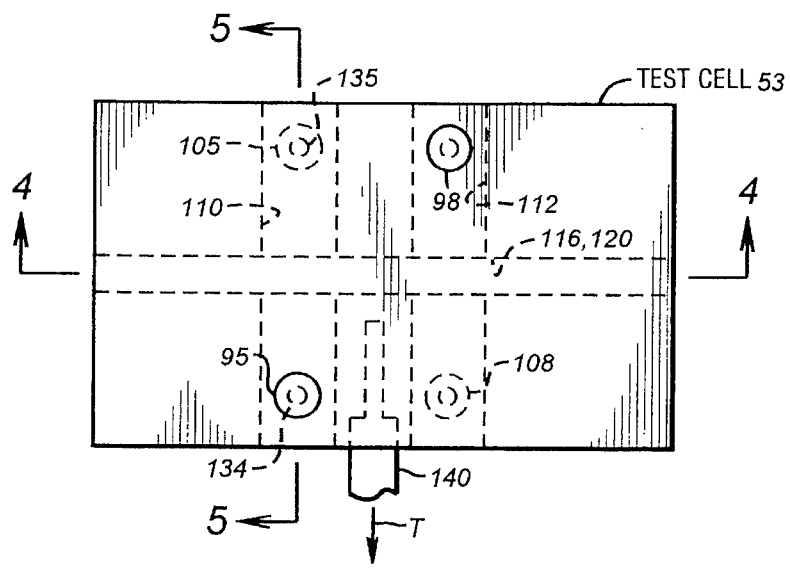
FIG. 3 is a drawing of the test cell shown in FIG. 2.

With reference to FIG. 3, there is shown test cell 53 having microwave entrance ports 95 and 98. On the other side of test cell 53 as represented by dash lines are microwave exit ports 105 and 108. Connecting microwave entrance port 95 and microwave exit port 105 is a microwave channel 110. Similarly a microwave channel 112 connects microwave entrance port 98 with microwave exit port 108. The distance between microwave ports 95 and 105 is the same as the distance between microwave ports 98 and 108. Thus, the distances between radiator antennas 63 and 65 and receiver antennas 67 and 70, respectively, are the same.

Figure 4:
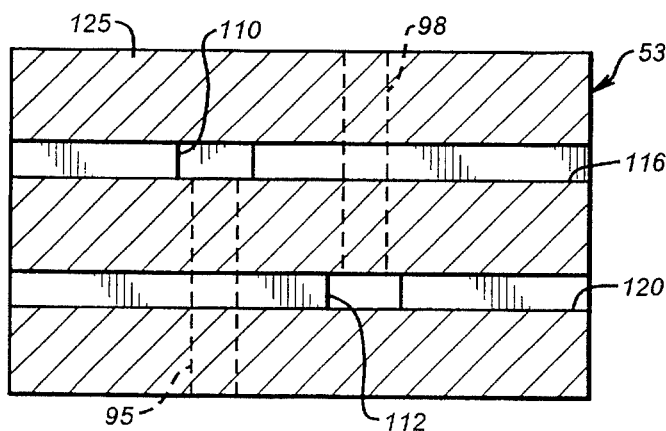
FIGS. 4 and 5 are cross-sections through the test cell shown in FIG. 3 and taken along lines 4—4 and 5—5, respectively.

Also shown in FIG. 3 are fluid channels 116 and 120. Since fluid channels 116 and 120 are in line in this view of test cell 53 only one set of dash lines represents them. This can be seen better in FIG. 4 which has a cut-away view of test cell 53 in the direction of the arrows 4—4. There is shown a body 125 which may be made of metal having fluid channels 116 and 120 passing through it longitudinally and microwave channels 110 and 112 for the microwave energy cut transversely through it. It should be noted that channels 110 and 112 are shown as being offset from each other. However, this offset is not necessary to the practice of the present invention.

It should also be noted that fluid channels 116, 120 have different rectangular cross-sections so that the microwave energy that passes through the fluids, have different distances of passage as noted hereinbefore and will be discussed hereinafter.

Figure 5:
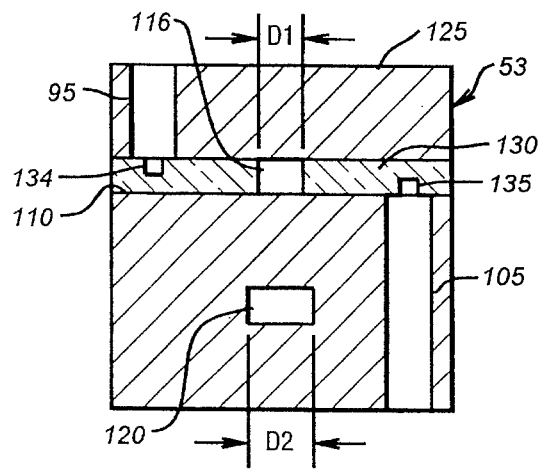

Referring to FIG. 5, there is a view of test cell 53 in the direction of 5—5, shown in FIG. 3. Channel 110 is filled with a solid material 130, such as high density teflon, that is conductive to microwave energy, except for that portion of channel 110 that forms a cross-section of fluid channel 116. Cut into body 125 is microwave entrance port 95. Further there is another chamber 134 which connects microwave entrance port 95 and enters into material 130 in channel 110. This is for the insertion of microwave antenna 63, which may be of the commercial type made by Omni Spectra, Part No. 2057-5134-02, slightly modified for the present application. Similarly, microwave exit port 105, for antenna 67, is shown with an additional chamber 135 which centers into material 130. Again, this is for the purpose of monitoring the sample stream. Basically, it is the same type of antenna as that entered into entrance port 95, but again modified for the present application. The microwave energy when applied to the antenna 63 enters material 130 and is directed to cross channel 116 until it reaches the antenna 67 inserted in exit port 105.

Fluid channels 116 and 20 have the same vertical distances which is dictated by the vertical distances of microwave channels 110 and 112. However, fluid channel 116 has a horizontal distance D1 while fluid channel 120 has a horizontal distance D2. Distance D2 in this example is greater than distance D1. However, the reverse could be true and present invention will still function properly.

For ease of explanation, we will hereinafter refer to the microwave energy path from antenna 63 to antenna 67 as the first side of cell 53 and the microwave energy path from antenna 65 to antenna 70 as the second side of cell 53.

Referring also to FIG. 2, lines 10 and 55 are connected in a conventional manner to fluid channel 116 so that the sample stream in line 10 will flow through test cell 53 to line 55. Similarly, lines 11 and 55 are connected to fluid channel 120 in such a manner that the sample stream in line 55 will enter fluid channel 120 and exit test cell 53 through line 11. Similarly antenna 67 in entrance port 98 is connected to line 66 and antenna 70 in exit port 108 is connected to line 67.

As can be seen in FIG. 3, temperature sensor 140, which is a thermocouple, is inserted into a chamber cut into block 105 and thus reads the temperature of block 105 as the temperature of the reference and as of the production stream sample.

The power and phase shift due to fluid in the second side are used as base line data in mini-computer means 40. The base line data and the test data derived from the petroleum sample stream are temperature corrected by computer means 40. Computer means 40 determines the water-cut in accordance with the corrected base line data, the corrected test data and look-up table stored in its memory.

The apparatus and method of the present invention determines the difference in phase shifts of the microwave energies due to the sample stream and not the difference in phase shifts due to portions of test cell 53 and the sample stream. As such, the phase shift difference due to diameter differences of the sample stream is less than 360° and is uniquely related to the water cut of the sample stream. As noted in detail hereinbefore, this is accomplished by having two different microwave measurements using two paths of different lengths due to different stream diameters for the microwave energy through the sample stream. This permits the use of simultaneous equations to eliminate the phase shifts due to portions of the test cell 53 as well as any full circle n*360° phase shift ambiguities. The following equations explain this concept in greater detail.

Referring also to FIG. 5, the following terms are used in equations:

$Q_f$ = total phase shift, due to fluid following in channel 116, from transmitter to receiver $Q_2$ = total phase shift, due to fluid flowing in channel 120, from transmitter to receiver $D_f$ = microwave energy path distance in channel 116

$D_2$ = microwave energy path distance in channel 120

$L_o$ = total distance between antennas $L$ = length of one teflon insert $E$ = dielectric constant
 $E_t$ = teflon dielectric constant
 $E_w$ = distilled water dielectric constant
 $E_a$ = air dielectric constant
 $E_v$ = vacuum dielectric constant
 $E_o$ = oil dielectric constant
 $E_f$ = any fluid mixture $W$ = wavelength in media of dielectric constant t,w,a,v,o,f $X_1$ = sample phase shift due to non-common path elements not utilizing channel 116 between the antennas $X_2$ = reference phase shift due to non-common path elements not between the antennas utilizing channel 120

$Y_o$ = total distance between antennas

A first phase shift with fluid of Ef dielectric in flowing through channels 116 and 120

$$Q_1 = X_1 + \frac{D1}{W_a} *360* [E_F \wedge .5] + \left[ \left( L_o - \frac{D1}{W_a} \right) \right] *360* E_t \wedge .5 \quad \text{EQ1}$$

Where the term $(D_1/W_a)*360*[E_f{}^{\wedge}0.5]$ represents the gap phase shift and the term $[(L_o-D_1)/W_a]*360*E_t{}^{\wedge}0.5$ represents the Teflon phase shift.

A second phase shift with fluid of $E_f$ dielectric in both sides $$Q_2 = X_2 + \frac{D2}{W_a} *360 [E_F \; .5] + \left[ \left( L_o - \frac{D2}{W_a} \right) \right] *360* E_t \wedge .5 \quad \text{EQ2}$$

Where the term $(D_2/W_a)*360*[Et^{0.5}]$ represents gap phase shift and the term $[(L_o-D_1/W_a]*360*E_t^{0.5}$ represents Teflon the phase shift.

The common mode effects such as $X_1-X_2$ and $n*360$ are eliminated by subtracting EQ1–EQ2 to yield:

$$DELQ = Q_1 - Q_2 = \left[ (D_1 - D_2) * \frac{360}{Wa} \right] * (E_F{}^\wedge.5 - E_t{}^\wedge.5) + (X_1 - X_2) \quad \text{EQ3}$$

Assume that $X_1-X_2$ is reduced to 0 by addition of a calibration constant $K_o$. A number of relationships between dielectrics and geometry can be derived from the above equations if certain combinations of fluids, $E_f$, are placed in the cell. By placing air into channels 116 and 120, we develop:

$$DELQa = Q_{1a} - Q_{2a} = \left[ (D_1 - D_2) * \frac{360}{WA} \right] * (E_o{}^\wedge.5 - E_t{}^\wedge.5) \quad \text{EQ4}$$

By placing oil into channels 116 and 120, we develop:

$$DELQ_o = Q_{1o} - Q_{2o} = \left[ (D_1 - D_2) * \frac{360}{WA} \right] * (E_o{}^\wedge.5 - E_t{}^\wedge.5) \quad \text{EQ5}$$

The effects of sensor geometry may be eliminated by division of EQ5 by EQ4 to yield $$\frac{DELQ_o}{DELQ_a} = \frac{(E_o{}^\wedge.5 - E_t{}^\wedge.5)}{(E_a{}^\wedge.5 - E_t{}^\wedge.5)} \quad \text{EQ6}$$

It should be noted that in general for any fluid relative to air EQ6 may be written as:

$$\frac{DELQ_f}{DELQ_a} = \frac{(E_f{}^\wedge.5 - E_t{}^\wedge.5)}{(E_a{}^\wedge.5 - E_t{}^\wedge.5)} \quad \text{EQ7}$$

By solving for fluid dielectric in terms of air and the ratio term we have EQ8

$$E_f = \left[ \left( \frac{DELQ_f}{DELQ_a} \right) * (E_a{}^\wedge.5 - Et{}^\wedge.5) + Et{}^\wedge.5 \right]^2 \quad \text{EQ8}$$

Where the constants are determined for the sensor cell in the lab and the variable $DELQ_f$ is determined at run time. EQ8 represents a true dielectric of a fluid mixture independent of sensor geometry.

Once true dielectric of a fluid mixture is obtained, there are many published methods of then using the known dielectric of each of two immiscible fluids and the mixture dielectric to calculate the emulsion (water continuous or oil continuous) and ratio of water and oil in the mixture. This calculation is of great value as the use of dielectric alone minimizes the need for complex and expensive calibration experiments.

The present invention may be subject to many modifications and changes without departing form the spirit or essential characteristics thereof. The present embodiment should therefor be considered in all respects as illustrative and not restrictive of the scope of the invention as defined by the appended claims.

What is claimed:

1. Apparatus which determines the water cut of a sample petroleum stream comprising:

means for irradiating the sample petroleum stream with microwave energy from first and second locations;

means defining first and second channels from said first and second locations, respectively, through which the microwave energy travels through the sample stream, said first and second channels being of different length;

means for receiving microwave energy from said first and second paths, respectively, after the microwave energies have passed through the sample stream, and providing first and second received signals corresponding thereto;

means for detecting the phase shifts of both the microwave energies after passage through the sample stream, means for forming the phase difference between the respective detected phase shifts and providing a signal corresponding thereto, and means for deriving the water cut from the derived phase differences signal.

2. Apparatus as described in claim 1 in which the means for defining first and second channels is a test cell having two fluid channels, one fluid channel being slightly wider than the other fluid channel, but not enough to cause a full 360° phase shift.

3. Apparatus as described in claim 1 in which the irradiating means includes:

a pair of transmitter means spatially arranged with the microwave channel for causing the microwave energies to flow through the microwave channel, and the receiver means includes a pair of receiver antenna means spatially arranged with the microwave channels for receiving the microwave energies passing through the microwave channels.

4. A method for determining the water cut of a sample petroleum stream comprising the steps of:

irradiating the sample petroleum stream with microwave energy over two radiation paths;

arranging the distance which the microwave energy travels through the sample stream along each radiation path so that one distance is greater than the other distance by an amount sufficient not to cause greater than a 360° phase shift;

receiving microwave energy from the two radiation paths after the microwaves have passed through the sample stream diametrically and generating signals corresponding to the received microwaves;

deriving the phase difference between the received microwaves and generating a phase difference signal representative thereof; and determining the water cut of the sample stream from the derived phase difference signal.

5. The method as described in claim 4 in which the arranging the distance step includes using a test cell having two different diameter cylindrical fluid channels, one fluid channel being wider than the other fluid channel.

* * * * *